United States Patent [19]

Ingram

[11] 4,326,742
[45] Apr. 27, 1982

[54] METHOD AND APPARATUS FOR INSERTING AND REMOVING SOFT CONTACT LENS

[76] Inventor: W. Frank Ingram, P.O. Box 23, Griffin, Ga. 30224

[21] Appl. No.: 141,602

[22] Filed: Apr. 18, 1980

[51] Int. Cl.³ .............................................. A61F 9/00
[52] U.S. Cl. ................................................. 294/1 CA
[58] Field of Search .................... 294/1 CA, 25, 64 R; 128/303 R

[56] References Cited

U.S. PATENT DOCUMENTS

| | | | |
|---|---|---|---|
| 3,697,109 | 10/1972 | Parrent | 294/1 CA |
| 4,126,345 | 11/1978 | List | 294/1 CA |
| 4,193,622 | 3/1980 | Overman | 294/1 CA |

Primary Examiner—James B. Marbert
Attorney, Agent, or Firm—Patrick F. Henry

[57] ABSTRACT

The apparatus comprises a frame which is positioned over the eyes in front of the forehead so that a recessed portion of the frame fits over the bridge of the nose. An arm pivoted on the frame to swing selectively from in front of one eye to the other, with adjustable stop means to limit the extent of motion, has a slot in the end to receive an insertion device which comprises a slotted collar removably fitted into the end of the swinging arm and supporting a spring biased shaft having a small cup thereon which temporarily retains the soft contact lens by surface tension and not by suction. The removing device comprises a multi-pronged tweezer having arms of stainless steel tipped with a small ball of latex and the arms expand or retract in response to finger movement.

To insert a soft contact lens, the spring loaded plunger is mounted in the groove of the swinging arm of the centering frame and the soft contact lens is placed on the rubber cup which is wet with a solution. With the centering frame worn like a pair of glasses, the insertion device is precisely centered over the cornea with the soft contact lens in the cup a few mm. from corneal surface, holding the lower eyelid down as far as comfortable the plunger is moved until the soft contact is in contact with the cornea and the plunger is released pulling the cup from the contact lens. To remove the contact lens, the removal device is placed in the slot of the swinging arm of the centering frame, the plunger is depressed so that the prongs open to about 15 mm. in diameter and while holding the prongs open the device is carefully moved toward the eye until the latex covered soft ends touch the cornea. The plunger is released causing the ends to close thereby retracting and grasping the soft contact lens causing it to buckle thereby breaking the surface tension and the lens is removed. There are different forms of the invention.

18 Claims, 9 Drawing Figures

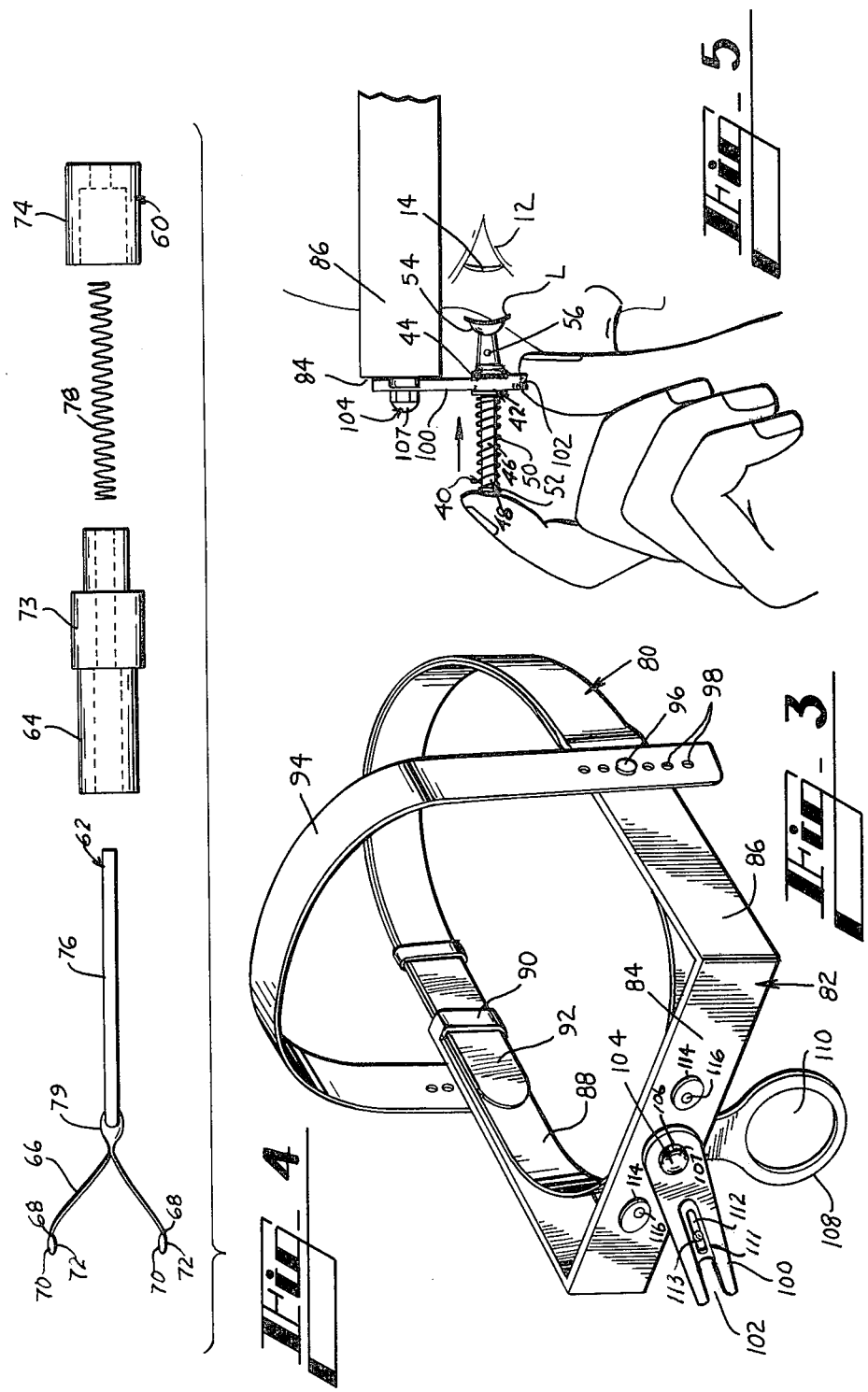

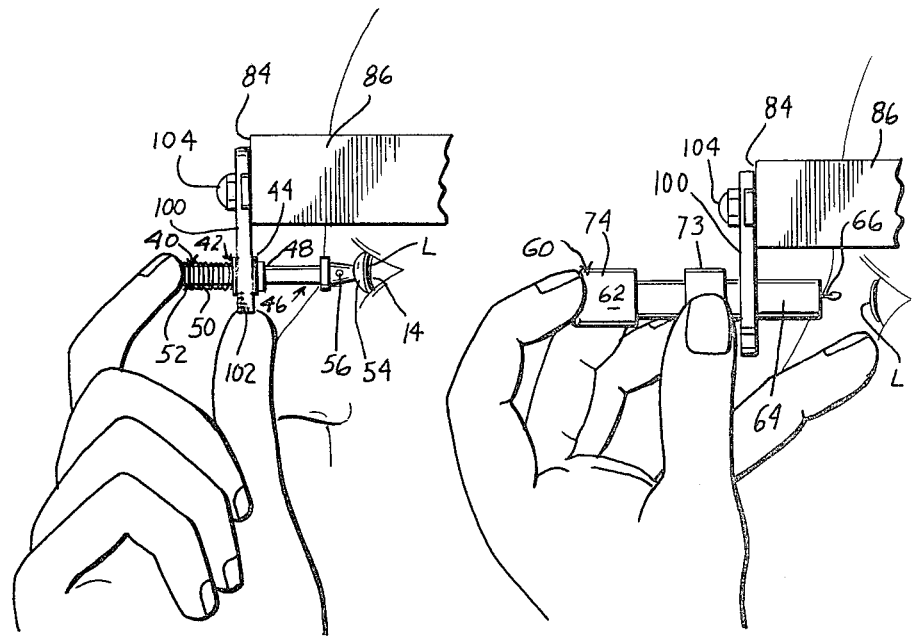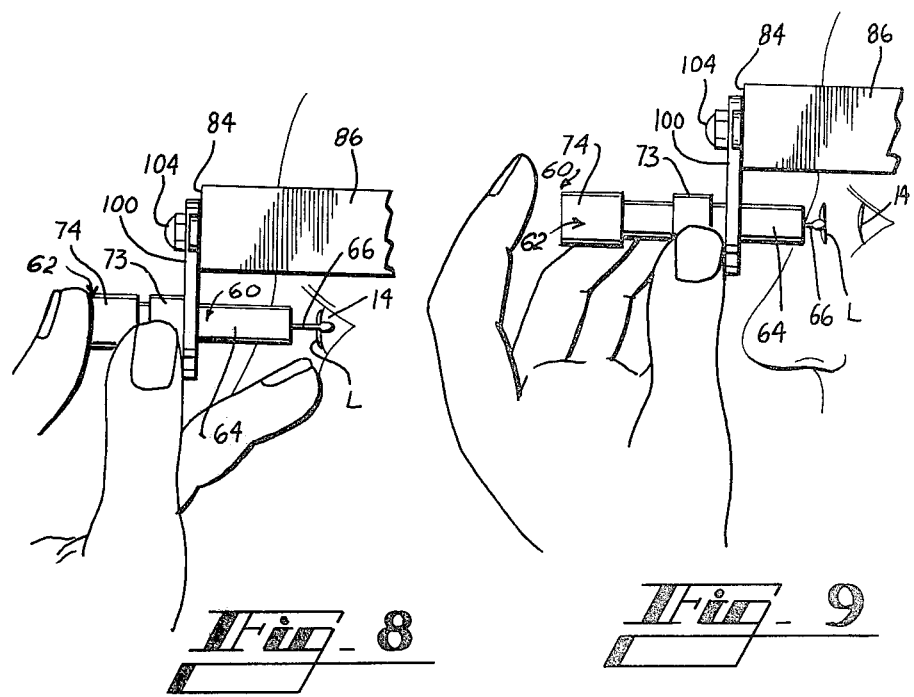

METHOD AND APPARATUS FOR INSERTING AND REMOVING SOFT CONTACT LENS

BACKGROUND OF THE INVENTION

1. Field of the Invention

Medicine and surgery, especially devices and implements for inserting and removing something from the eye. Eyeglasses and especially contact lens and devices for manipulating same.

2. Description of the Prior Art

Soft contact lens, which are made of a pliable plastic as opposed to the hard or rigid corneal contact lens, are frequently worn by persons who have had cataract operations. Such persons often have difficulty in inserting and removing the soft contact lens. Also, elderly persons, and in fact anyone who has some sort of impaired vision or manual dexterity due to a variety of reasons such as arthritis, palsy condition, injury and so forth, encounter difficulty in inserting and removing a soft contact lens. Indeed, it is sometimes virtually impossible for such persons to perform this seemingly simple operation alone but objectionable to have someone else put something in their eyes. Ordinary suction cup devices, tweezer apparatus and the like which are sometimes used in conjunction with hard contact lens do not alone solve this problem. Suction cups are hard to release. Tweezers are hard to manipulate. Furthermore, it is not practical for a wearer of soft contact lens to have someone else assist each time in inserting and removing soft contact lens.

One version of the present method and apparatus provides a frame which is worn somewhat like conventional eyeglasses but with open spaces in front of the eyes so that the soft contact lens may be readily positioned directly in front of the center of the eye and the lens moved into engagement with the surface of the eye in a gentle but effective manner. The frame is lightweight and inexpensive and can be provided with an optional monocular lens to assist in location. The device may be worn by means of side frame members like eyeglasses or can be held in place by a headband of elastic material or the like.

A primary object of this invention is to provide a means for the positioning, alignment and insertion of a soft contact lens and for the removal thereof.

Another object of this invention is to provide a relatively lightweight, inexpensive frame arrangement which temporarily holds, positions, aligns and facilitates inserting of a soft contact lens by manual manipulation and also provides a means for removal of the lens.

Still another object of this invention resides in the use of a small cup plunger device for insertion and the substitution of a removal device comprising small tweezers which are actuated by a slight plunger movement.

Another object of the headband form of the invention resides in the pre-setting of the device for repetitive use by the same person and always in proper alignment for the eyes.

Other and further objects and advantages of this invention will become apparent upon reading the following description of a preferred embodiment taken in conjunction with the accompanying drawings.

BRIEF DESCRIPTION OF THE DRAWINGS

FIG. 3 is a perspective view of a modified and second version of the invention employing an optional monocular lens and a headband.

FIG. 4 is a dissembled elevation view of the soft contact lens removal device.

FIG. 5 is a side elevation view of the insertion device positioned by the centering frame on the device in FIG. 3 and having a soft contact lens thereon for movement to the eye.

FIG. 6 is a side elevation view similar to FIG. 5 but with the insertion device extended to place the soft contact lens on the corneal surface.

FIG. 7 is a side elevation view of the removal device as it would be positioned in the centering frame of FIG. 3 and extended with the prongs open just about to move towards and touch the cornea to grasp the soft contact lens.

FIG. 8 is a side elevation view similar to FIG. 7 but with the prongs closed on the soft contact lens and partially retracted for removing the lens from the corneal surface.

FIG. 9 is a diagrammatic view similar to FIG. 8 showing a two-prong removal device collapsing and grasping the soft contact lens and retracting same for removal.

DESCRIPTION OF A PREFERRED EMBODIMENT

Figure 1:
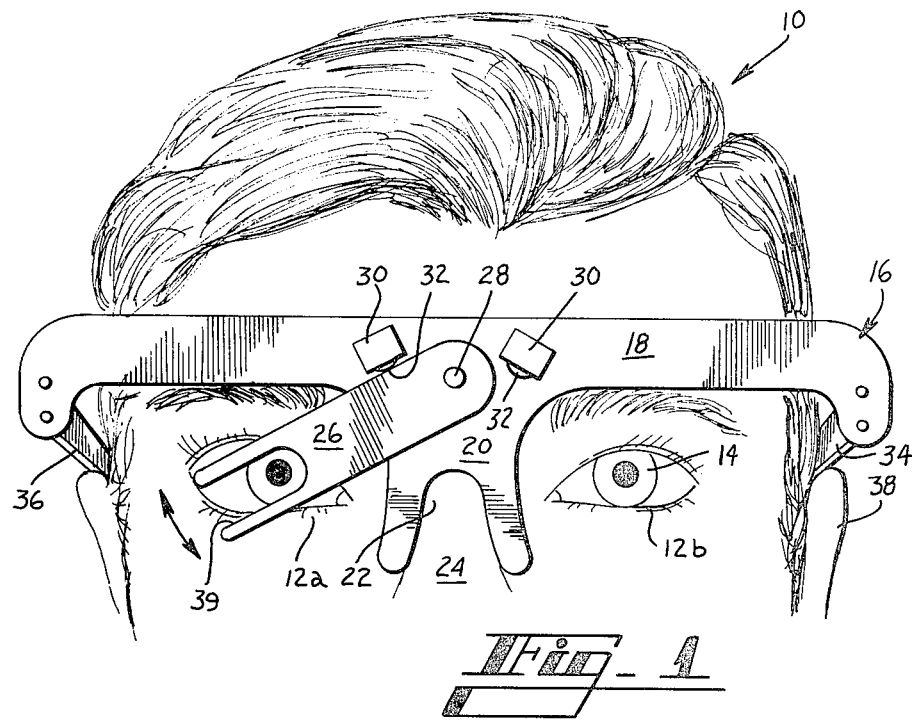
FIG. 1 is a front view of one form of the invention shown in place on the head and on the eyes.

In FIG. 1 there is shown generally the head 10 of a person having eyes 12a and 12b with respective corneas 14 which are to receive soft contact lens L and to have same removed therefrom.

The first version of the means for aligning, inserting and removing the contact lens L comprises a first light centering frame 16 that may be manufactured from lightweight metal or plastic and which comprises a support member 18 normally worn in front of the face and in front of the forehead over the eyes as shown in FIG. 1, there being a nose plate 20 thereon having a nose cavity 22 therein to fit over the nose bridge 24 thereby centering the frame 16 and the member 18 over the respective eyes 12. The lightweight arm 26 is pivotally mounted on pivot pin 28 on member 18 to swing from in front of one eye 12a to a position in front of the other eye 12b selectively manually operated by the person who is inserting and removing the soft contact lens. Adjustable stops on member 18 comprise fixed blocks 30 having small adjustment screws 32 which may be moved from one position to another to align and stop the arm 26 in the desired position with respect to eyes 12a and b. Adjustment screws 32 may be adjusted and set for each person's particular facial shapes and distances and may remain that way until the device is used by some other person.

Frame 16 is provided with respective side retaining members 34, 36, similar to those on ordinary eyeglasses, which are connected to the member 18 and which may fit over the ears 38 or may be spring tensioned to remain in place on the side of head 10. In any event, the device 16 will only be worn for a very short period of time and can be quickly removed.

The soft contact lens L insertion means is a device 40 shown in FIG. 5 and which may be mounted on the arm 26 in an end slot 39 or in the headband version shown in FIG. 3 which will be described later. Insertion means 40 comprises a collar 42 having peripheral flanges 44 and supporting for movement thereon a plunger 46 comprising a plunger shaft 48 which is spring biased by a coil spring 50 retained by a small end retainer 52. The end of plunger 48 has a small rubber cup 54 attached thereto and there is a small air opening 56 leading to the interior of cup 54 to prevent permanent suction therein so that the cup 54 holds lens L temporarily by surface tension rather than pressure which the cup 54 is easily dislodged from lens L once lens L is on the fluid of the eye 12a or 12b and the surface tension holds the lens L to the eye 12a or 12b. The collar 42 has a groove between the flanges 44 which would removably receive the arm 26.

The soft contact lens L removal means 60 is a multipronged tweezer or tong device 62, some of which are disclosed in one or more of the following U.S. Pat. Nos.: 987,173; 1,578,800; 2,919,696; 3,481,641; 3,628,824. However, the present removal means 60 may be manufactured from plastic or nylon and employs a hollow sleeve or barrel 64 inside of which are two small stainless steel, curved arms 66 having respective ends 68 extending outside of the sleeve 64 with terminal bent tips 70. Each tip 70 of the present device 62 is a small stainless steel ball approximately 1 mm. in diameter which are enlarged by building up latex to approximately 3 mm in diameter which provides a larger ball 72 having a soft, atraumatic surface which is harmless to the cornea. The hollow sleeve 64 is provided with a collar 73 and a cylindrical actuator 74 attached to a reduced portion 75 of sleeve 64 which supports a shaft 76 operating against a coil spring 78 inside portion 76 and actuator 74 to selectively extend or retract the arms 66 and respective end 68 simultaneously in order to open and release when extended outside sleeve 64 and to retract and grasp when retracted inside sleeve 64. Actuator 74 and the shaft 76 perform as a plunger which is operated to extend the tips 70 approximately 15 mm apart in diameter and while open the entire 2 tips 70 in open position until the latex covered end 72 touch the cornea. The plunger actuator 74 is released and it retracts grasping the lens L causing it to buckle thereby breaking the surface tension whereby the lens is then pulled away from the eye upon retraction. Removal means 60 will function on either form shown in FIGS. 1 and 2 or FIGS. 3 thru 9.

The head frame for centering and holding the insertion and removal devices for soft contact lens shown in FIGS. 3 thru 9 is especially suited for those persons who have difficulty in manipulating the lens into the center of the eye on the cornea and also may have difficulty in seeing through the eyes due to a cataract operation. Some persons due to age, arthritis or other such ailments are unable to manipulate the hands and fingers. The head frame device 80 in FIG. 3 comprises a rigid front 82 having a front member 84 and side members 86 connected together to make a rigid front frame which fits about the forehead. Members 84 and 86 may be nylon or other suitable material such as plastic. A flexible headband 88 is attached to the inside of the frame 82 and comprises a strap arrangement having strap loops 90 and a terminal tongue 92 which may be inserted for adjustment. The headband 88 is attached in place by a flexible top head member 94 which extends across the top of the head and is fastened through the side members 86 and the headband 88 by means of removable screws 96 through selective openings 98 in the head strap 94.

The front of front frame member 84 is provided with a swing arm 100 having a slot 102 therein and being pivotally attached to the front member 84 by a removable pivot pin arrangement 104 which comprises a plastic bearing ring 106 and a cap nut 107. The swing arm 100 is adjustable for holding and centering the soft contact lens insertion and removable devices. The pivot arrangement 104 also holds an optional swinging lens holder 108 having a cataract lens +12–15 plano-convex lens 110 therein which is swingable from one eye to the other so that the lens 110 may be used with one eye while locating the soft contact lens for insertion or for removing same. An adjustment plate 111 on swing arm 100 has a slot 112 thereon adjustable on a screw 113 to position the lens and adjust above or below the eye.

The swing arm 100 is adjusted into position for an individual by means of cam type adjustment and stop members 114 each comprising a small disc of nylon or the like which is pivoted off-center on a respective pivot pin 116 so that the travel of the swing arm may be limited as desired and selected by the individual wearer and set in place so that each time the swing arm will stop in the proper position for the centering and insertion of the soft contact lens or removal thereof.

Figure 2:
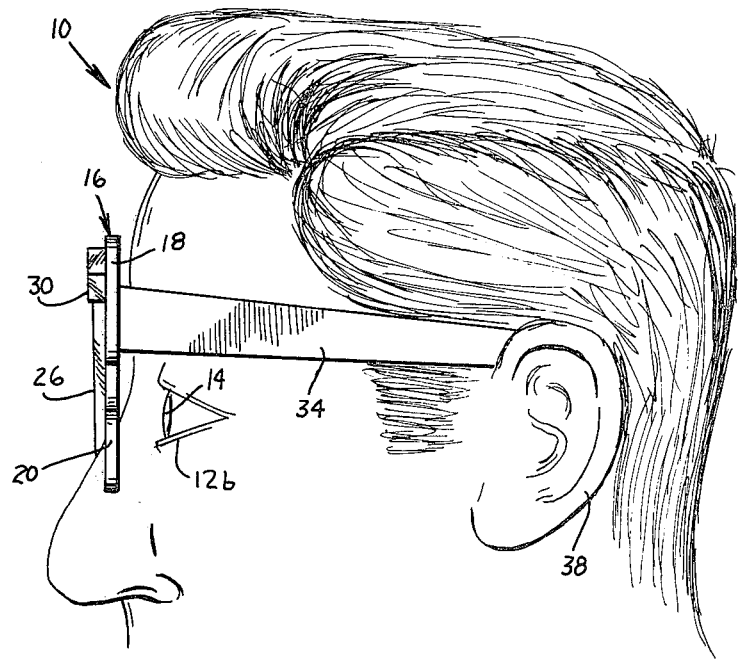
FIG. 2 is a side elevation view of the device shown in FIG. 1.

In the operation of the device 80 the same insertion means 40 shown in FIGS. 5 and 6, inclusive, may be used with the first embodiment of FIGS. 1 and 2 and function the same in either embodiment as described previously. Likewise, the same removal means 60 shown in FIGS. 7 thru 9 may be used with the first embodiment of FIGS. 1 and 2 and function the same in either embodiment as described previously.

While I have shown and described two embodiments this is by way of illustration only and various alterations, changes, revisions, variations, omissions and departures may be made in the embodiments shown without departing from the scope of my invention as defined only by a proper interpretation of the appended claims.

What is claimed:
 1. In an apparatus for inserting and removing soft contact lens:
  a frame for head support on the head in front of the eyes and forehead of a person, support means mounted on the frame to move selectively from in front of one eye to the other, adjustable means for limiting the extent of moving of said support means for adjusting same to position the arm substantially in front of the center of the cornea of the eye, said support means removably retaining selectively a contact lens insertion means and a removal means thereon.
 2. The device in claim 1 including:
  said insertion means comprising a contact lens retaining means and extension and retraction means for moving same into engagement with and away from the cornea of the eye.
 3. The device in claim 1 including:
  said removal means being selectively positionable to substitute for said insertion means and vice versa and said removal means comprising a multipronged tweezer having resilient arms of stainless steel or the like and each being tipped with a small, soft ball formed from latex, plastic or the like.
 4. The device in claim 2: said insertion means comprising a plunger having said insertion means retaining means thereon, spring means resisting the movement of said plunger toward said eye, means for temporarily supporting a soft contact lens, and means for attaching said plunger to said support means.

5. The device in claim 4: said means for temporarily supporting being a flexible cup and said means for attaching comprising a collar having a groove therein to be fitted on the arm.

6. The device in claim 3, said removal means comprising a support means for attachment on and detachment from said pivoted support means, a plunger means mounted on said support means, and soft tips on said plunger to be opened and closed to release or grasp said soft contact lens.

7. The device in claim 6 wherein said support means comprises a support member having said plunger movable therein, said tips being on small spring arms attached to said plunger and movable into and out of said support member for opening or closing said tips.

8. The device in claim 1 wherein said frame includes an adjustable means extending around the head of the person, and a second adjustable means extending across the top of the head of the person whereby the frame may be adjusted on the head to place the frame in front of the eyes.

9. The device in claim 8: said pivoted support means comprising a pivoted arm having a slot therein, said adjustable means for limiting on said front of said frame being for adjusting and setting the movement of the arm, whereby said insertion means or said removal means may be positioned by insertion into the slot on said arm.

10. The device claimed in claim 1 wherein there is a monocular lens mounted on said frame and movable from one eye to the other to assist in inserting or removing the contact lens.

11. The device in claim 1, wherein said frame comprises a front nose member which is fitted over the nose, an arm pivotally mounted on said frame, stop limit means for said arm, a slot in said arm, and side members on said frame for retaining same in position on each side of the head of the person.

12. The device claimed in claim 11, wherein said stop members comprise a pair of fixed members each having a movable member thereon.

13. The device in claim 8: said arm having a movable plate thereon, a slot in said plate, and a screw on said arm for adjusting said plate to adjust the depth of the slot in the arm whereby the position of the insertion or removal means may be adjusted above or below the center of the eye.

14. In a device for grasping and removing a soft contact lens:
a plunger mounted for extension or retraction, a pair of spring arms mounted on said plunger and each arm having a tip thereon, the tip of each arm being provided with a soft cushion of material such as latex rubber and the like for grasping a contact lens positioned on the eye, an elongated sleeve having a bore therethrough, said plunger being mounted for movement in said bore, spring means normally biasing said plunger toward extended position, and an actuating member mounted on one end of said plunger for moving same whereby said spring arms may be moved inside said sleeve to bring same together or released outside said sleeve to permit same to open further apart to release said contact lens.

15. A device for positioning and releasing a soft contact lens to the eye comprising:
a support means to be mounted on a frame or the like positioned on the head of a person for positioning or removing a soft contact lens, a plunger mounted on said support means, spring means resisting the movement of said plunger toward said eye, a cup member mounted on said plunger for supporting a soft contact lens thereon, and means for supporting said cup on said plunger.

16. The device claimed in claim 15, wherein said support means comprises a collar having a slot therein, and a passageway leading from said cup to the outside whereby said cup is prevented from creating excessive suction on said soft contact lens.

17. In a method for inserting and removing soft contact lens from the eyes of a person:
supporting a support means on the person's head in front of the eyes, positioning a contact lens insertion means on said support means, said contact insertion means comprising a contact lens retainer and means for extending and retracting same on said frame into engagement with the cornea of the eye, positioning a contact lens on said contact lens retainer, and inserting same against the cornea of the eye and releasing same to the eye, and moving the insertion means selectively from in front of one eye to the other.

18. The method claimed in claim 17 including substituting a soft contact lens removal means on said frame, said contact lens removal means comprising a multi-pronged grasping device having soft tips thereon, extending said removal device to said soft contact lens on the eye, opening the soft tips, closing the soft tips to buckle said lens, grasping the lens in the tips and retracting same from the eye.

* * * * *